(12) United States Patent
Ouyang et al.

(10) Patent No.: US 12,257,141 B2
(45) Date of Patent: *Mar. 25, 2025

(54) PREPARATION METHOD FOR THREE-LAYER ARTIFICIAL BLOOD VESSEL AND APPLICATION THEREOF

(71) Applicant: WUHAN YOUNGSEN BIOTECH CO., LTD., Wuhan (CN)

(72) Inventors: Chenxi Ouyang, Wuhan (CN); Jiarong Li, Wuhan (CN); Chenhong Wang, Wuhan (CN); Sishi Liu, Wuhan (CN); Jianpeng Liu, Wuhan (CN)

(73) Assignee: WUHAN YOUNGSEN BIOTECH CO., LTD., Wuhan (CN)

( * ) Notice: Subject to any disclaimer, the term of this patent is extended or adjusted under 35 U.S.C. 154(b) by 778 days.

This patent is subject to a terminal disclaimer.

(21) Appl. No.: 17/377,427

(22) Filed: Jul. 16, 2021

(65) Prior Publication Data

US 2021/0338410 A1 Nov. 4, 2021

Related U.S. Application Data

(63) Continuation of application No. PCT/CN2020/072101, filed on Jan. 14, 2020.

(30) Foreign Application Priority Data

Jan. 16, 2019 (CN) .......................... 201910040739.8
Jan. 16, 2019 (CN) .......................... 201910040748.7
Jan. 16, 2019 (CN) .......................... 201910040750.4

(51) Int. Cl.
| | | |
|---|---|---|
| D01D 1/02 | (2006.01) | |
| A61F 2/00 | (2006.01) | |
| A61F 2/06 | (2013.01) | |
| B05D 1/00 | (2006.01) | |
| D01D 5/00 | (2006.01) | |
| D01D 10/02 | (2006.01) | |
| D04H 1/728 | (2012.01) | |
| B05D 1/02 | (2006.01) | |
| B29C 48/151 | (2019.01) | |

(52) U.S. Cl.
CPC .............. *A61F 2/06* (2013.01); *A61F 2/0077* (2013.01); *A61F 2/062* (2013.01); *B05D 1/002* (2013.01); *D01D 5/003* (2013.01); *D01D 5/0038* (2013.01); *D01D 5/0061* (2013.01); *D01D 5/0084* (2013.01); *D04H 1/728* (2013.01); *A61F 2002/0081* (2013.01); *A61F 2210/0076* (2013.01); *A61F 2240/001* (2013.01); *A61F 2250/0058* (2013.01); *A61L 2420/02* (2013.01); *B05D 1/02* (2013.01); *B05D 2254/02* (2013.01); *B05D 2503/00* (2013.01); *B05D 2518/00* (2013.01); *B29C 48/151* (2019.02); *D10B 2331/04* (2013.01); *D10B 2331/041* (2013.01); *D10B 2331/10* (2013.01); *D10B 2509/00* (2013.01)

(58) Field of Classification Search
CPC ....... A61F 2210/0076; A61F 2240/001; A61L 2420/02; B05D 1/002; B05D 1/02; B05D 2254/02; B05D 2503/00; B05D 2518/00; D01D 1/02; D01D 5/0038; D01D 5/0084; D01D 10/02; D10B 2331/04; D10B 2331/041; D10B 2331/10
USPC .... 264/171.1, 172.19, 173.1, 234, 255, 258, 264/331.11, 331.19, 331.21, 465; 427/2.25, 481

See application file for complete search history.

(56) References Cited

U.S. PATENT DOCUMENTS

2013/0253663 A1* 9/2013 Amoroso ................ A61L 27/48
623/23.75

FOREIGN PATENT DOCUMENTS

| CN | 103474610 A | * | 12/2013 | ............. D04H 1/728 |
| CN | 104414772 A | | 3/2015 | |
| CN | 106540327 A | | 3/2017 | |
| CN | 109914036 A | * | 6/2019 | ............. D04H 1/728 |

OTHER PUBLICATIONS

Translation of CN 103474610 A (published on Dec. 25, 2013).*
Translation of CN 106540327 A (published on Mar. 29, 2017).*

* cited by examiner

*Primary Examiner* — Leo B Tentoni
(74) *Attorney, Agent, or Firm* — JEEN IP LAW, LLC (57) ABSTRACT

The present invention provides a preparation method preparation method for three-layer artificial blood vessel and application thereof. The three-layer artificial blood vessel comprise three layers, electrospinning inner layer, dense middle layer and electrospinning outer layer, the three-layer structure is closely combined and difficult to separate. The inner layer with a cytoskeleton-like structure can promote the formation of intima; the dense middle layer can effectively prevent the leakage of biomacromolecules and increase the puncture resistance of the whole artificial blood vessel; and the outer layer can promote the growth of tissue cells and better integrate with tissue. The three-layer artificial blood vessel provided by the invention has excellent blood compatibility, good flexibility, good puncture resistance and interlayer peeling resistance. The preparation method is convenient and is suitable for industrial scale production.

7 Claims, 3 Drawing Sheets

PREPARATION METHOD FOR THREE-LAYER ARTIFICIAL BLOOD VESSEL AND APPLICATION THEREOF

CROSS-REFERENCE TO RELATED APPLICATIONS

The present application is a continuation-application of International Patent Application (PCT) No. PCT/CN2020/072101 filed on Jan. 14, 2020, which claims foreign priority of three Chinese Patent Applications, No. 201910040739.8, No. 201910040748.7 and No. 201910040750.4 filed on Jan. 16, 2019, the entire contents of which are hereby incorporated by reference.

TECHNICAL FIELD

The present invention relates to the technical field of medical materials, in particular to a preparation method for three-layer artificial blood vessel and application thereof.

BACKGROUND ART

After an artificial polytetrafluoroethylene blood vessel which is clinically applied is implanted to a human body, thrombus is easy to form, and a punctured artificial polytetrafluoroethylene blood vessel is relatively large in pore so as to easily result in blood oozing. Therefore, various problems in terms of long-time patency rate, blood oozing resistance and puncture resistance more need to be solved in a development process of a small-diameter blood vessel.

The blood vessels of human body are three layers structure containing inner, middle and outer layers. People are trying to fabricate double-layer or multi-layer artificial blood vessels in different ways to simulate the structure and performance of human blood vessels as much as possible. At present, expanded polytetrafluoroethylene is the main material for artificial blood vessels, such as Gore (China machinery injection 20153462072) use expanded polytetrafluoroethylene inside and outside double layers, and the middle layer is low permeable silica gel layer. However, the pores in the inner and outer layers are small, and it is difficult for endothelial cells to adhere and grow, resulting in the blood vessel cannot be perfectly fused with human tissue. In the prior art, there are artificial blood vessels with multilayer structure, the combination between the layers is not tight, and the blood exudates from the fibrous space of the layers, which easily leads to the separation between the layers, that is, pseudoaneurysm appears in clinic.

SUMMARY

A main purpose of the present invention is to overcome the defects of the application of the artificial blood vessel in prior art, and to provide a preparation method for three-layer artificial blood vessel and application thereof. In the three-layer artificial blood vessel, the inner layer with a cytoskeleton-like structure can promote the formation of intima; and the dense middle layer can effectively prevent the leakage of biomacromolecules and increase the puncture resistance of the whole artificial blood vessel; and the outer layer can promote the growth of tissue cells and better integrate with tissue.

In order to achieve the above-mentioned purpose, the present invention provides a preparation method for three-layer artificial blood vessel, including the following steps:

S1: dissolving a macromolecular compound into a solvent to obtain an electrospinning solution with a concentration of 5-30% w/v and an electric-spray solution with a concentration of 10-60% w/v;

S2: placing the electrospinning solution obtained in S1 over a mandrel device and performing electrospinning to obtain a porous electrospun inner layer, drying the inner layer to remove the residual solvent;

S3: with the inner layer obtained in S2 as a receiving surface, performing first electric spray, second electric spray, . . . $n^{th}$ electric spray with the electric-spray solution to obtain a dense middle layer, wherein the first electric spray process includes spraying, stopping, spraying, stopping, . . . repeated cycles, a time of the stopping in the first electric spray process is 5-20 min; and a time of each of the first electric spray, the second electric spray and the $n^{th}$ electric spray is 5-50 min; and S4: with the dense middle layer obtained in S3 as a receiving surface, performing electrospinning, and then drying to obtain the three-layer artificial blood vessel.

In some embodiments of the invention, in S1, the macromolecular compound is selected from one or more of polycaprolactone (PCL), polyurethane (PU) and polylactide (PLA); and the solvent is selected from one or more of N,N-dimethylformamide (DMF), N,N-dimethylacetamide (DMAC), acetone, tetrahydrofuran (THF) and hexafluoroisopropanol (HFIP); and a weight-average molecular weight of the polycaprolactone, the polylactide and the polyurethane is 10000-1000000.

Preferably, the weight-average molecular weight of the PCL is 60000-300000, the weight-average molecular weight of the PLA is 50000-500000, and the weight-average molecular weight of the PU is 100000-600000.

In some embodiments of the invention, the macromolecular compound for preparing electric-spray solution is selected from one or two of the polycaprolactone and the polyurethane.

In some embodiments of the invention, in S2 and S4, the step of performing electrospinning includes: regulating a distance between a spinning nozzle and a mandrel receiving device to be 5-30 cm; and performing spinning under the conditions that an ambient temperature is 15-70° C., ambient humidity is 15-70% RH, a voltage is regulated to be 10-50 kV, a feeding speed of the solution is 0.1-5 mL/h, and a rotating speed of a roller is 50-1000 rad/min.

In some embodiments of the invention, an electrospinning time in S2 is 5-30 h and an electrospinning time in S4 is 0.5-15 h.

In some embodiments of the invention, in S3, an n value for the $n^{th}$ electric spray is greater than or equal to 3. Preferably, the n value for the $n^{th}$ spray is 3-8. There is still a great deal of solvent even in a high-concentration spinning solution, and a quantity of the solution attached to surfaces of fibers can be properly controlled by single electric spray within short time. However, a solute contained by single electric spray is not enough to completely cover the surfaces of the fibers to form a dense membrane with a certain thickness, so that the electric spray needs to be repeated intermittently for many times to achieve the aim of complete coverage and meanwhile to ensure that there is enough time for the volatilization of the solvent in the electric spray solution.

In some embodiments of the invention, in S3, concentrations of the electric-spray solution for the first electric spray, the second electric spray and the $n^{th}$ electric spray are sequentially increased. The concentration should be within a range which can be accepted by an electric spray technology, that is, the solution can be sprayed under the traction of an electric field. In addition, firstly, a low-concentration solution with relatively high flowability is electrically sprayed for many times, so that the electrically sprayed solution is in tight and seamless contact with the fibers; after the electrically sprayed solution is dried, a high-concentration solution is electrically sprayed to reduce solvent adhesion, and meanwhile, the dense membrane with a certain thickness is achieved within relatively short time.

Preferably, the concentrations of the electric-spray solution in the first electric spray, the second electric spray and the $n^{th}$ electric spray are respectively 15-35% w/v, 20-40% w/v and 30-60% w/v.

In some embodiments of the invention, in S3, the first electric spray, the second electric spray and the $n^{th}$ electric spray are performed under the conditions including: the feeding speed is 0.1-5 mL/h, the rotating speed of the roller is 50-1000 rad/min; and the ambient temperature is 10-50° C., the ambient humidity is 10-60% RH, and the voltage is 5-30 kV.

Further, the present invention provides a three-layer artificial blood vessel prepared by using the above-mentioned preparation method, comprising an electrospun inner layer, an electric-spray dense middle layer and an electrospun outer layer.

In some embodiments of the invention, a thickness of the inner layer is 1 μm-1000 μm, a thickness of the outer layer is 1 μm-500 μm, diameters of the fibers in the inner layer and the outer layer are 50 nm-5000 nm, and a thickness of the dense middle layer is 1 μm-1000 μm;

preferably, the thickness of the inner layer is 5 μm-700 μm, the thickness of the outer layer is 5 μm-500 μm, diameters of the fibers in the inner layer and the outer layer are 50 nm-3000 nm, and the thickness of the dense middle layer is 5 μm-700 μm; and
  more preferably, the thickness of the inner layer is 50 μm-450 μm, the thickness of the outer layer is 50 μm-300 μm, diameters of the fibers in the inner layer and the outer layer are 800 nm-3000 nm, and the thickness of the dense middle layer is 10 μm-300 μm.

The three-layer artificial blood vessel further provided by the present invention is applicable to an in-vivo vascular graft surgery, arteriovenous fistula or a heart bypass surgery.

In the prior art, the electrospinning technology is used to prepare the artificial blood vessel with multilayer fiber structure. However, due to the large gap between the layers, the blood will seep out from the fiber gap of a layer and cause layers to peel off (pseudoaneurysm).

Found by an applicant through research, in order to obtain an artificial blood vessel with excellent properties, it is necessary to reasonably select the material of a blood vessel and optimize and control a structure. An inner layer structure of an artificial composite blood vessel is prepared by adopting an electrospinning technology to obtain a microstructure promoting the generation of an endangium, thereby achieving the long-time patency rate; and meanwhile, the unique blood vessel structure brought by the electrospinning technology ensures that good mechanical properties may be still maintained after the wall of the blood vessel is punctured for many times.

Electric spray means aggregation on the surfaces of the fibers, and therefore, the fibers in an inner layer which is in contact with an electric spray layer are fused to achieve the effect of tight contact with the fibers in the inner layer. By virtue of the characteristics of trace solution spray in an electric spray technology and low solvent content in a high-concentration solution, the solution sprayed on the inner layer is only enough to fuse the fibers on the outermost surface of the inner layer, but cannot further fuse deep-layer fibers on the inner layer. A preliminary micro-permeable layer is formed after an electric spray solution is dried, at the moment, the porosity of the micro-permeable layer has been greatly reduced as comparison with that of the fibers on the inner layer; and then, trace solution spray is repeated to gradually reduce the porosity of the micro-permeable layer until pores are eliminated, and then, a solution spray quantity is increased to complete electric spray of the structure of the dense middle layer. Finally, the outer layer was obtained by electrospinning on the surface of the dense middle layer, so as to obtain the three-layer artificial blood vessel with three layers of electrospinning inner layer, dense middle layer and electrospinning outer layer, the three-layer structure is closely combined and difficult to separate. The inner layer with a cytoskeleton-like structure can promote the formation of intima; the dense middle layer can effectively prevent the leakage of biomacromolecules and increase the puncture resistance of the whole artificial blood vessel; and the outer layer can promote the growth of tissue cells and better integrate with tissue.

The three-layer artificial blood vessel provided by the invention has excellent blood compatibility, good flexibility, good puncture resistance and interlayer peeling resistance. The preparation method is convenient and is suitable for industrial scale production.

DETAILED DESCRIPTION

The present invention will be described below in detail in conjunction with the accompanying drawings and specific embodiments. All materials used in the embodiments are available commercially.

Definitions

Puncture resistance, there is no accurate general definition of this performance in the world at present. This application is tested with reference to the pharmaceutical industry standard YY0500-2004/ISO7198:1998 of China. It is mentioned in the standard that when artificial blood vessels are clinically designed for vascular access, it is necessary to measure the residual strength of blood vessels after repeated puncture. The puncture tool used in the embodiments of the application is: 16 G puncture needle (ISO 9626:2016 Stainless steel needle tubing for the manufacture of medical devices—Requirements and test methods).

Embodiment 1: Preparation Process of Three-Layer Artificial Blood Vessel (1) Preparation of a solution:

PCL (the weight-average molecular weight is 100000) and PU (the weight-average molecular weight is 120000) are dissolved into HFIP, wherein a weight ratio of the PCL to the PU is equal to 10:90, and the dissolved product is heated and stirred in a 40° C. water bath for 12 h to obtain a polymer solution with the concentration of 8% w/v for standby application of electrospinning.

PU (the weight-average molecular weight is 150000) is dissolved into a mixed solvent of N,N-dimethylformamide (DMF) and acetone (a volume ratio is 5/5) and is heated and stirred in a 40° C. water bath for 12 h to obtain electric spray solutions with concentrations of 18% w/v, 24% w/v and 40% w/v for standby application of electric spray.

(2) Electrospinning: the solution obtained in (1) is injected into a 10 mL injector which is added with a 21 G stainless steel syringe needle. A distance between a spinning nozzle and a roller (mandrel receiving device) is regulated to be 12 cm, and spinning is performed for 18 h under the conditions that the ambient temperature is 40° C., the ambient humidity is 40% RH, the voltage is regulated to be 30 kV, the rotating speed of the roller is 100 rad/min, and the feeding speed of the solution is 1 mL/h to obtain an electrospun inner layer.

(3) A fiber membrane of the electrospun inner layer obtained in (2) is dried for 12 h to remove the excessive residual solvent.

(4) Electric Spray:
  a) Set electric spray conditions that the concentration of the polymer solution to be 18% (w/v), the feeding speed to be 3.0 mL/h, the rotating speed of the roller to be 50 rad/min, the ambient temperature to be 50° C., the ambient humidity to be 50% RH and the voltage to be 30 kV, perform the electric spray for 30 min, stop for 20 min. When a trace amount of electric spray solution is attached to surfaces of fibers on an inner layer and is fused with the fibers, the porosity of the fiber layer is reduced.
  b) Perform the electric spray for 30 min again, and then stop for 20 min, so that the electric spray solution is secondarily fused with the fibers, and the porosity is further reduced.
  c) Regulate the concentration to be 24% (w/v), the feeding speed to be 4 mL/h and the rotating speed of the roller to be 50 rad/min, perform the electric spray for 10 min to eliminate the porosity and form a relatively thin dense electric spray membrane.
  d) Regulate the concentration to be 40% (w/v), the feeding speed to be 0.1 mL/h and the rotating speed of the roller to be 80 rad/min, perform the electric spray for 30 min to ensure that the electric spray solution is aggregated on the surface of the relatively thin dense electric spray membrane, and dry to form a dense middle layer with a certain thickness.

(5) A dense middle layer obtained in (4) is used as a receiving surface, perform the electrospinning like step (2) for 5 h and then dry for more than 12 h to obtain an electrospun outer layer, and finally, the artificial blood vessel with a three-layer composite structure is obtained, named Three-Layer Artificial Blood Vessel.

Figure 1A:
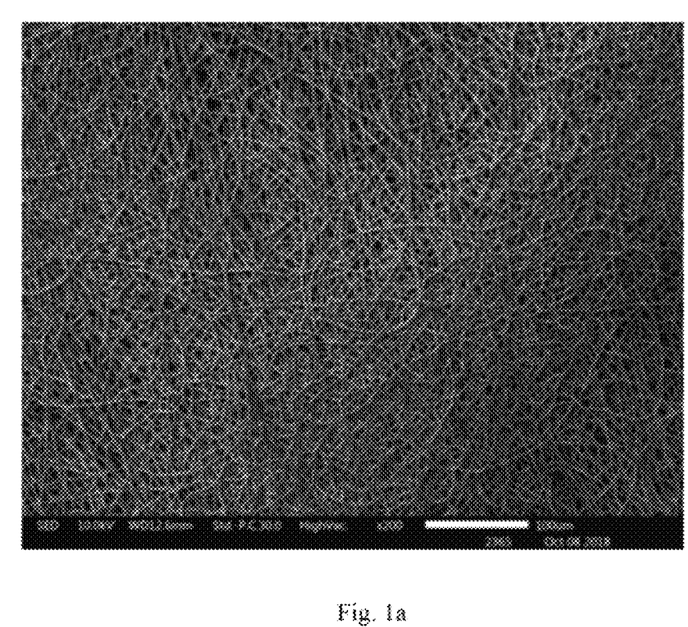
FIG. 1 is schematic diagram showing an SEM of a fiber morphology of an electrospun inner layer and an electrospun outer layer of the three-layer artificial blood vessel achieved in embodiment 1.
Figure 1B:
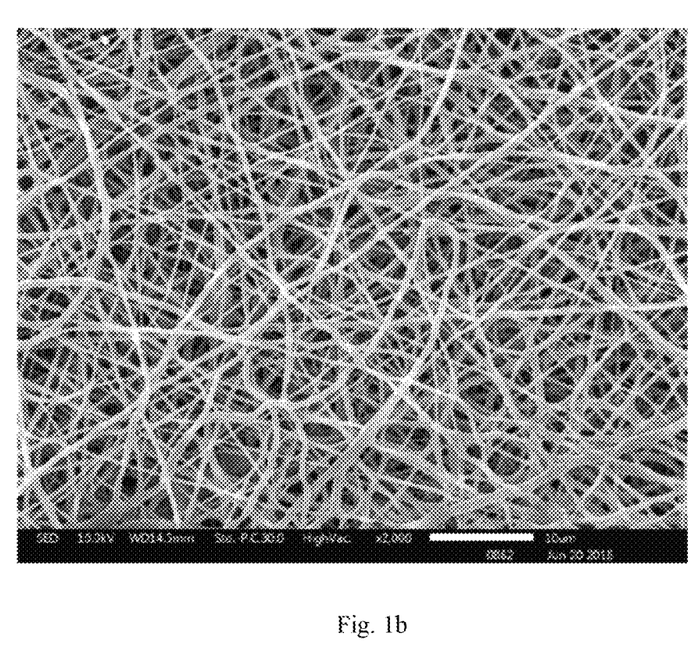
Figure 2:
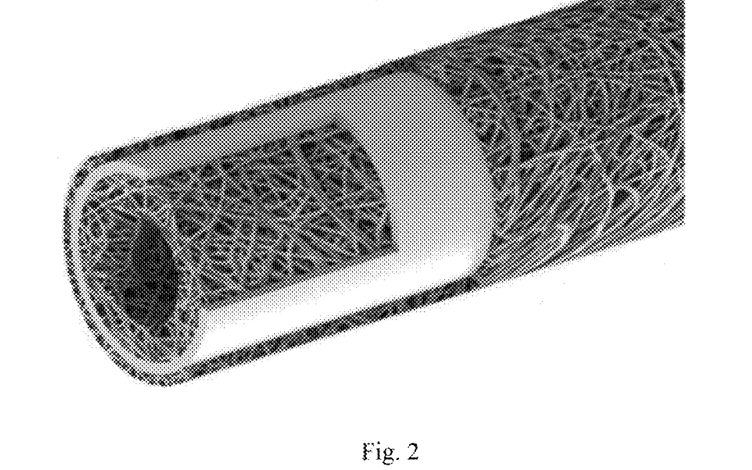
FIG. 2 is a schematic diagram showing an SEM of the three-layer artificial blood vessel achieved in embodiment 1.

FIG. 1 is schematic diagram showing an SEM of a fiber morphology of an electrospun inner layer and an electrospun outer layer of the three-layer artificial blood vessel achieved in embodiment 1 (FIG. 1a is the electrospun inner layer; FIG. 1b is the electrospun outer layer). FIG. 2 is a schematic diagram showing an SEM of the three-layer artificial blood vessel achieved in embodiment 1. By measurement, a thickness of the electrospun inner layer is 450 μm, a thickness of an electrospun outer layer is 300 μm, diameters of fibers of the inner layer and the outer layer are 800 nm, and a thickness of the dense middle layer is 300 μm.

Embodiment 2: Preparation Process of Three-Layer Artificial Blood Vessel (1) Preparation of a solution:

PCL (the weight-average molecular weight is 100000) and PU (the weight-average molecular weight is 200000) are dissolved into HFIP, wherein a weight ratio of the PCL to the PU is equal to 10:90, and the dissolved product is heated and stirred in a 40° C. water bath for 12 h to obtain a polymer solution with the concentration of 15% w/v for standby application of electrospinning.

PU (the weight-average molecular weight is 150000) is dissolved into a mixed solvent of N,N-dimethylformamide (DMF) and acetone (a volume ratio is 5/5) and is heated and stirred in a 40° C. water bath for 12 h to obtain electric spray solutions with concentrations of 35% w/v, 40% w/v and 55% w/v for standby application of electric spray.

(2) Electrospinning: the solution obtained in (1) is injected into a 10 mL injector which is added with a 21 G stainless steel syringe needle. A distance between a spinning nozzle and a roller (mandrel receiving device) is regulated to be 18 cm, and spinning is performed for 15 h under the conditions that the ambient temperature is 40° C., the ambient humidity is 40% RH, the voltage is regulated to be 20 kV, the rotating speed of the roller is 120 rad/min, and the feeding speed of the solution is 1 mL/h to obtain an electrospun inner layer.

(3) A fiber membrane of the electrospun inner layer obtained in (2) is dried for 12 h to remove the excessive residual solvent.

(4) Electric Spray:
  a) Set electric spray conditions that the concentration of the polymer solution to be 35% (w/v), the feeding speed to be 0.2 mL/h, the rotating speed of the roller to be 800 rad/min, the ambient temperature to be 10° C., the ambient humidity to be 20% RH and the voltage to be 5 kV, perform the electric spray for 15 min, stop for 10 min. When a trace amount of electric spray solution is attached to surfaces of fibers on an inner layer and is fused with the fibers, the porosity of the fiber layer is reduced.
  b) Perform the electric spray for 15 min again, and then stop for 10 min, so that the electric spray solution is secondarily fused with the fibers, and the porosity is further reduced.
  c) Regulate the concentration to be 40% (w/v), the feeding speed to be 0.1 mL/h and the rotating speed of the roller to be 300 rad/min, perform the electric spray for 5 min to eliminate the porosity and form a relatively thin dense electric spray membrane.
  d) Regulate the concentration to be 55% (w/v), the feeding speed to be 1.5 mL/h and the rotating speed of the roller to be 600 rad/min, perform the electric spray for 20 min to ensure that the electric spray solution is aggregated on the surface of the relatively thin dense electric spray membrane, and dry to form a dense middle layer with a certain thickness.

(5) A dense middle layer obtained in (4) is used as a receiving surface, perform the electrospinning like step (2) for 6 h and then dry for more than 12 h to obtain an electrospun outer layer, and finally, the Three-Layer Artificial Blood Vessel is obtained.

Figure 3:
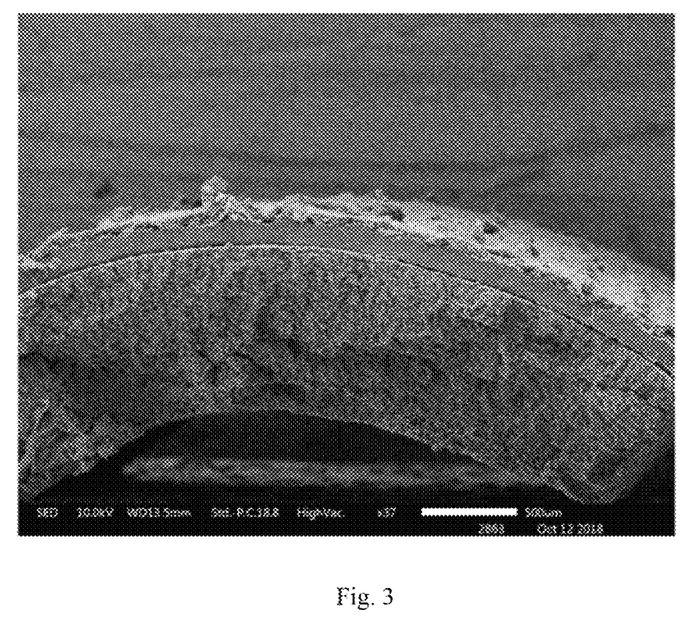
FIG. 3 is schematic diagram showing a cross-sectional SEM of the three-layer artificial blood vessel achieved in embodiment 2.

FIG. 3 is schematic diagram showing a cross-sectional SEM of the three-layer artificial blood vessel achieved in embodiment 2. By measurement, a thickness of the electrospun inner layer 50 μm, a thickness of an electrospun outer layer is 50 μm, diameters of fibers of the inner layer and the outer layer are 3000 nm, and a thickness of the dense middle layer is 10 μm.

Embodiment 3: Preparation Process of Three-Layer Artificial Blood Vessel (1) Preparation of a solution:

PLA (the weight-average molecular weight is 150000), PCL (the weight-average molecular weight is 120000) and PU (the weight-average molecular weight is 150000) are dissolved into HFIP, wherein a weight ratio of the PLA:PCL:PU=5:5:90, and the dissolved product is heated and stirred in a 40° C. water bath for 10 h to obtain a polymer solution with the concentration of 20% w/v for standby application of electrospinning.

PU (the weight-average molecular weight is 200000) is dissolved into a mixed solvent of N,N-dimethylformamide (DMF) and acetone (a volume ratio is 6/4) and is heated and stirred in a 40° C. water bath for 10 h to obtain electric spray solutions with concentrations of 35% w/v, 40% w/v and 50% w/v for standby application of electric spray.

(2) Electrospinning: the solution obtained in (1) is injected into a 10 mL injector which is added with a 21 G stainless steel syringe needle. A distance between a spinning nozzle and a roller (mandrel receiving device) is regulated to be 20 cm, and spinning is performed for 15 h under the conditions that the ambient temperature is 40° C., the ambient humidity is 40% RH, the voltage is regulated to be 20 kV, the rotating speed of the roller is 100 rad/min, and the feeding speed of the solution is 1 mL/h to obtain an electrospun inner layer.

(3) A fiber membrane of the electrospun inner layer obtained in (2) is dried for 12 h to remove the excessive residual solvent.

(4) Electric Spray:

a) Set electric spray conditions that the concentration of the polymer solution to be 35% (w/v), the feeding speed to be 3.5 mL/h, the rotating speed of the roller to be 1000 rad/min, the ambient temperature to be 20° C., the ambient humidity to be 10% RH and the voltage to be 5 kV, perform the electric spray for 20 min, stop for 5 min. When a trace amount of electric spray solution is attached to surfaces of fibers on an inner layer and is fused with the fibers, the porosity of the fiber layer is reduced.

b) Perform the electric spray for 20 min again, and then stop for 5 min, so that the electric spray solution is secondarily fused with the fibers, and the porosity is further reduced.

c) Regulate the concentration to be 40% (w/v), the feeding speed to be 2.8 mL/h and the rotating speed of the roller to be 80 rad/min, perform the electric spray for 10 min to eliminate the porosity and form a relatively thin dense electric spray membrane.

d) Regulate the concentration to be 50% (w/v), the feeding speed to be 1.2 mL/h and the rotating speed of the roller to be 200 rad/min, perform the electric spray for 30 min to ensure that the electric spray solution is aggregated on the surface of the relatively thin dense electric spray membrane, and dry to form a dense middle layer with a certain thickness.

(5) A dense middle layer obtained in (4) is used as a receiving surface, perform the electrospinning like step (2) for 8 h and then dry for more than 12 h to obtain an electrospun outer layer, and finally, the Three-Layer Artificial Blood Vessel is obtained.

By measurement, a thickness of the electrospun inner layer 100 μm, a thickness of an electrospun outer layer is 100 μm, diameters of fibers of the inner layer and the outer layer are 2000 nm, and a thickness of the dense middle layer is 80 μm.

Embodiment 4: Preparation Process of Three-Layer Artificial Blood Vessel (1) Preparation of a solution:

PU (the weight-average molecular weight is 150000) are dissolved into a mixed solvent of N,N-dimethylacetamide (DMAC) and acetone (a volume ratio is 5/5) is heated and stirred in a 40° C. water bath for 12 h to obtain a polymer solution with the concentration of 15% w/v for standby application of electrospinning.

PU (the weight-average molecular weight is 150000) is dissolved into a mixed solvent of N,N-dimethylacetamide (DMAC) and acetone (a volume ratio is 5/5) and is heated and stirred in a 35° C. water bath for 12 h to obtain electric spray solutions with concentrations of 25% w/v, 35% w/v and 50% w/v for standby application of electric spray.

(2) Electrospinning: the solution obtained in (1) is injected into a 10 mL injector which is added with a 21 G stainless steel syringe needle. A distance between a spinning nozzle and a roller (mandrel receiving device) is regulated to be 8 cm, and spinning is performed for 17 h under the conditions that the ambient temperature is 45° C., the ambient humidity is 30% RH, the voltage is regulated to be 25 kV, the rotating speed of the roller is 150 rad/min, and the feeding speed of the solution is 1 mL/h to obtain an electrospun inner layer.

(3) A fiber membrane of the electrospun inner layer obtained in (2) is dried for 12 h to remove the excessive residual solvent.

(4) Electric Spray:

a) Set electric spray conditions that the concentration of the polymer solution to be 25% (w/v), the feeding speed to be 0.2 mL/h, the rotating speed of the roller to be 60 rad/min, the ambient temperature to be 30° C., the ambient humidity to be 10% RH and the voltage to be 30 kV, perform the electric spray for 15 min, stop for 10 min. When a trace amount of electric spray solution is attached to surfaces of fibers on an inner layer and is fused with the fibers, the porosity of the fiber layer is reduced.

b) Perform the electric spray for 15 min again, and then stop for 10 min, so that the electric spray solution is secondarily fused with the fibers, and the porosity is further reduced.

c) Regulate the concentration to be 35% (w/v), the feeding speed to be 1.8 mL/h and the rotating speed of the roller to be 150 rad/min, perform the electric spray for 20 min to eliminate the porosity and form a relatively thin dense electric spray membrane.

d) Regulate the concentration to be 50% (w/v), the feeding speed to be 0.5 mL/h and the rotating speed of the roller to be 700 rad/min, perform the electric spray for 30 min to ensure that the electric spray solution is aggregated on the surface of the relatively thin dense electric spray membrane, and dry to form a dense middle layer with a certain thickness.

(5) A dense middle layer obtained in (4) is used as a receiving surface, perform the electrospinning like step (2) for 4 h and then dry for more than 12 h to obtain an electrospun outer layer, and finally, the Three-Layer Artificial Blood Vessel is obtained.

By measurement, a thickness of the electrospun inner layer 200 μm, a thickness of an electrospun outer layer is 150 μm, diameters of fibers of the inner layer and the outer layer are 1000 nm, and a thickness of the dense middle layer is 100 μm.

Embodiment 5: Preparation Process of Three-Layer Artificial Blood Vessel (1) Preparation of a solution:

PLA (the weight-average molecular weight is 200000) and PU (the weight-average molecular weight is 150000) are dissolved into a mixed solvent of N,N-dimethylacetamide (DMAC) and acetone (a volume ratio is 5/5), wherein a weight ratio of the PLA:PU=5:95, and the dissolved product is heated and stirred in a 40° C. water bath for 12 h to obtain a polymer solution with the concentration of 20% w/v for standby application of electrospinning.

PU (the weight-average molecular weight is 120000) is dissolved into a mixed solvent of N,N-dimethylacetamide (DMAC) and acetone (a volume ratio is 6/4) and is heated and stirred in a 35° C. water bath for 12 h to obtain electric spray solutions with concentrations of 30% w/v, 40% w/v and 60% w/v for standby application of electric spray.

(2) Electrospinning: the solution obtained in (1) is injected into a 10 mL injector which is added with a 21 G stainless steel syringe needle. A distance between a spinning nozzle and a roller (mandrel receiving device) is regulated to be 30 cm, and spinning is performed for 8 h under the conditions that the ambient temperature is 45° C., the ambient humidity is 35% RH, the voltage is regulated to be 30 kV, the rotating speed of the roller is 150 rad/min, and the feeding speed of the solution is 1 mL/h to obtain an electrospun inner layer.

(3) A fiber membrane of the electrospun inner layer obtained in (2) is dried for 12 h to remove the excessive residual solvent.

(4) Electric Spray:
a) Set electric spray conditions that the concentration of the polymer solution to be 30% (w/v), the feeding speed to be 0.5 mL/h, the rotating speed of the roller to be 1000 rad/min, the ambient temperature to be 30° C., the ambient humidity to be 30% RH and the voltage to be 10 kV, perform the electric spray for 5 min, stop for 10 min. When a trace amount of electric spray solution is attached to surfaces of fibers on an inner layer and is fused with the fibers, the porosity of the fiber layer is reduced.
b) Perform the electric spray for 10 min again, and then stop for 10 min, so that the electric spray solution is secondarily fused with the fibers, and the porosity is further reduced.
c) Regulate the concentration to be 40% (w/v), the feeding speed to be 3.8 mL/h and the rotating speed of the roller to be 550 rad/min, perform the electric spray for 5 min to eliminate the porosity and form a relatively thin dense electric spray membrane.
d) Regulate the concentration to be 60% (w/v), the feeding speed to be 4.5 mL/h and the rotating speed of the roller to be 800 rad/min, perform the electric spray for 5 min to ensure that the electric spray solution is aggregated on the surface of the relatively thin dense electric spray membrane, and dry to form a dense middle layer with a certain thickness.

(5) A dense middle layer obtained in (4) is used as a receiving surface, perform the electrospinning like step (2) for 3 h and then dry for more than 12 h to obtain an electrospun outer layer, and finally, the Three-Layer Artificial Blood Vessel is obtained.

By measurement, a thickness of the electrospun inner layer 50 μm, a thickness of an electrospun outer layer is 50 μm, diameters of fibers of the inner layer and the outer layer are 1500 nm, and a thickness of the dense middle layer is 50 μm.

Embodiment 6: Preparation Process of Three-Layer Artificial Blood Vessel (1) Preparation of a solution:

PLA (the weight-average molecular weight is 500000) and PU (the weight-average molecular weight is 600000) are dissolved into a mixed solvent of N,N-dimethylacetamide (DMAC) and acetone (a volume ratio is 5/5), wherein a weight ratio of the PLA:PU=10:85, and the dissolved product is heated and stirred in a 40° C. water bath for 12 h to obtain a polymer solution with the concentration of 30% w/v for standby application of electrospinning.

PU (the weight-average molecular weight is 500000) is dissolved into a mixed solvent of N,N-dimethylacetamide (DMAC) and acetone (a volume ratio is 6/4) and is heated and stirred in a 35° C. water bath for 12 h to obtain electric spray solutions with concentrations of 20% w/v, 35% w/v and 50% w/v for standby application of electric spray.

(2) Electrospinning: the solution obtained in (1) is injected into a 10 mL injector which is added with a 21 G stainless steel syringe needle. A distance between a spinning nozzle and a roller (mandrel receiving device) is regulated to be 5 cm, and spinning is performed for 30 h under the conditions that the ambient temperature is 50° C., the ambient humidity is 50% RH, the voltage is regulated to be 40 kV, the rotating speed of the roller is 500 rad/min, and the feeding speed of the solution is 2 mL/h to obtain an electrospun inner layer.

(3) A fiber membrane of the electrospun inner layer obtained in (2) is dried for 12 h to remove the excessive residual solvent.

(4) Electric Spray:
a) Set electric spray conditions that the concentration of the polymer solution to be 20% (w/v), the feeding speed to be 2.5 mL/h, the rotating speed of the roller to be 800 rad/min, the ambient temperature to be 30° C., the ambient humidity to be 30% RH and the voltage to be 10 kV, perform the electric spray for 40 min, stop for 20 min. When a trace amount of electric spray solution is attached to surfaces of fibers on an inner layer and is fused with the fibers, the porosity of the fiber layer is reduced.
b) Perform the electric spray for 40 min again, and then stop for 15 min, so that the electric spray solution is secondarily fused with the fibers, and the porosity is further reduced.

c) Regulate the concentration to be 35% (w/v), the feeding speed to be 0.5 mL/h and the rotating speed of the roller to be 100 rad/min, perform the electric spray for 25 min to eliminate the porosity and form a relatively thin dense electric spray membrane.

d) Regulate the concentration to be 50% (w/v), the feeding speed to be 5.0 mL/h and the rotating speed of the roller to be 1000 rad/min, perform the electric spray for 20 min to ensure that the electric spray solution is aggregated on the surface of the relatively thin dense electric spray membrane, and dry to form a dense middle layer with a certain thickness.

(5) A dense middle layer obtained in (4) is used as a receiving surface, perform the electrospinning like step (2) for 15 h and then dry for more than 12 h to obtain an electrospun outer layer, and finally, the Three-Layer Artificial Blood Vessel is obtained.

By measurement, a thickness of the electrospun inner layer 200 μm, a thickness of an electrospun outer layer is 300 μm, diameters of fibers of the inner layer and the outer layer are 800 nm, and a thickness of the dense middle layer is 120 μm.

Embodiment 7: Preparation Process of Three-Layer Artificial Blood Vessel (1) Preparation of a solution:

PLA (the weight-average molecular weight is 50000), PCL (the weight-average molecular weight is 60000) and PU (the weight-average molecular weight is 100000) are dissolved into HFIP, wherein a weight ratio of the PLA:PCL:PU=5:10:85, and the dissolved product is heated and stirred in a 40° C. water bath for 10 h to obtain a polymer solution with the concentration of 12% w/v for standby application of electrospinning.

PU (the weight-average molecular weight is 100000) is dissolved into a mixed solvent of N,N-dimethylformamide (DMF) and acetone (a volume ratio is 6/4) and is heated and stirred in a 40° C. water bath for 10 h to obtain electric spray solutions with concentrations of 35% w/v, 40% w/v and 50% w/v for standby application of electric spray.

(2) Electrospinning: the solution obtained in (1) is injected into a 10 mL injector which is added with a 21 G stainless steel syringe needle. A distance between a spinning nozzle and a roller (mandrel receiving device) is regulated to be 5 cm, and spinning is performed for 8 h under the conditions that the ambient temperature is 15° C., the ambient humidity is 15% RH, the voltage is regulated to be 10 kV, the rotating speed of the roller is 50 rad/min, and the feeding speed of the solution is 0.1 mL/h to obtain an electrospun inner layer.

(3) A fiber membrane of the electrospun inner layer obtained in (2) is dried for 12 h to remove the excessive residual solvent.

(4) Electric Spray:

a) Set electric spray conditions that the concentration of the polymer solution to be 35% (w/v), the feeding speed to be 5 mL/h, the rotating speed of the roller to be 1000 rad/min, the ambient temperature to be 20° C., the ambient humidity to be 10% RH and the voltage to be 5 kV, perform the electric spray for 20 min, stop for 5 min. When a trace amount of electric spray solution is attached to surfaces of fibers on an inner layer and is fused with the fibers, the porosity of the fiber layer is reduced.

b) Perform the electric spray for 20 min again, and then stop for 5 min, so that the electric spray solution is secondarily fused with the fibers, and the porosity is further reduced.

c) Regulate the concentration to be 40% (w/v), the feeding speed to be 2.8 mL/h and the rotating speed of the roller to be 80 rad/min, perform the electric spray for 10 min to eliminate the porosity and form a relatively thin dense electric spray membrane.

d) Regulate the concentration to be 50% (w/v), the feeding speed to be 1.2 mL/h and the rotating speed of the roller to be 200 rad/min, perform the electric spray for 30 min to ensure that the electric spray solution is aggregated on the surface of the relatively thin dense electric spray membrane, and dry to form a dense middle layer with a certain thickness.

(5) A dense middle layer obtained in (4) is used as a receiving surface, perform the electrospinning like step (2) for 1 h and then dry for more than 12 h to obtain an electrospun outer layer, and finally, the Three-Layer Artificial Blood Vessel is obtained.

By measurement, a thickness of the electrospun inner layer 100 μm, a thickness of an electrospun outer layer is 50 μm, diameters of fibers of the inner layer and the outer layer are 1800 nm, and a thickness of the dense middle layer is 10 μm.

Comparative Example 1 (Comparison for Puncture Resistance of Puncture-Resistant Blood Vessel and Three-Layer Blood Vessel)

Sample 1: a puncture-resistant artificial blood vessel (double-layer structure) of which the preparation method is described as follows:

(1) Preparation of a solution:

PCL (the weight-average molecular weight is 100000) and PU (the weight-average molecular weight is 120000) are dissolved into HFIP, wherein a weight ratio of the PCL to the PU is equal to 10:90, and the dissolved product is heated and stirred in a 40° C. water bath for 12 h to obtain a polymer solution with the concentration of 10% w/v for standby application of electrospinning.

PU (the weight-average molecular weight is 150000) is dissolved into a mixed solvent of N,N-dimethylformamide (DMF) and acetone (a volume ratio is 5/5) and is heated and stirred in a 40° C. water bath for 12 h to obtain electric spray solutions with concentrations of 15% w/v, 18% w/v and 22% w/v for standby application of electric spray.

(2) Electrospinning: the solution obtained in (1) is injected into a 10 mL injector which is added with a 21 G stainless steel syringe needle. A distance between a spinning nozzle and a roller (mandrel receiving device) is regulated to be 15 cm, and spinning is performed for 8 h under the conditions that the ambient temperature is 40° C., the ambient humidity is 40% RH, the voltage is regulated to be 30 kV, the rotating speed of the roller is 100 rad/min, and the feeding speed of the solution is 1 mL/h to obtain an electrospun inner layer.

(3) A fiber membrane of the electrospun inner layer obtained in (2) is dried for 12 h to remove the excessive residual solvent.

(4) Electric Spray:

a) Set electric spray conditions that the concentration of the polymer solution to be 15% (w/v), the feeding speed to be 3.0 mL/h, the rotating speed of the roller to be 50 rad/min, the ambient temperature to be 50° C., the ambient humidity to be 50% RH and the voltage to be 30 kV, perform the electric spray for 30 min, stop for 20 min. When a trace amount of electric spray solution is attached to surfaces of fibers on an inner layer and is fused with the fibers, the porosity of the fiber layer is reduced.

b) Perform the electric spray for 30 min again, and then stop for 20 min, so that the electric spray solution is secondarily fused with the fibers, and the porosity is further reduced.

c) Regulate the concentration to be 18% (w/v), the feeding speed to be 4 mL/h and the rotating speed of the roller to be 50 rad/min, perform the electric spray for 10 min to eliminate the porosity and form a relatively thin dense electric spray membrane.

d) Regulate the concentration to be 22% (w/v), the feeding speed to be 0.1 mL/h and the rotating speed of the roller to be 80 rad/min, perform the electric spray for 30 min to ensure that the electric spray solution is aggregated on the surface of the relatively thin dense electric spray membrane, and dry to form a dense outer layer with a certain thickness.

By measurement, a thickness of the electrospun inner layer is 450 μm, diameters of the fibers are 800 nm, and a thickness of the dense outer layer is 300 μm.

Sample 2: a three-layer blood vessel of which the preparation method is the same as that in embodiment 1

Equipment: A 16 G puncture needle is selected for puncture.

Figure 4:
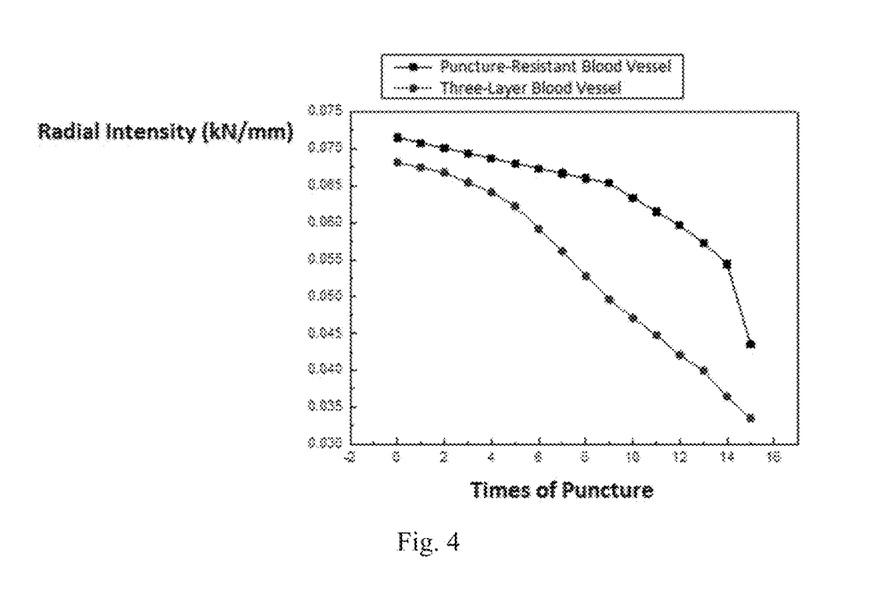
FIG. 4 is a diagram showing comparison for puncture times and mechanical properties of a puncture-resistant artificial blood vessel and an three-layer artificial blood vessel.

Differences of the two samples are shown as follows:

(0.07142 kN/mm) is higher than that of the three-layer blood vessel (0.06814 kN/mm). After the puncture is repeated for 15 times, the average radial intensity of the puncture-resistant blood vessel (0.04351 kN/mm) is higher than that of the three-layer blood vessel (0.03352 kN/mm), as shown in FIG. 4. Result shows that increasing the thickness of the dense layer can improve the puncture-resistant ability of multilayer artificial blood vessels. But the data show that the puncture resistance of three-layer blood vessels can also meet the clinical demands.

Furthermore, the three-layer blood vessels have other advantages, by adding a protective layer (an electrospun outer layer) outside the dense middle layer, the dense middle layer is not easy to slide relative to the inner layer, and the structure of the three-layer blood vessel structure is more stable. Compared with the two-layer structure, the three-layer blood vessel has stronger resistance to interlayer peeling. The three-layer artificial blood vessel obtained in embodiments 1-5 of the invention are respectively used in in vivo blood vessel transplantation and heart bypass surgery. After a period of practical application, it is confirmed that there is no peeling between layers (no pseudoaneurysm); the three-layer blood vessels of the invention can be perfectly fused with the human tissue without thrombosis and other complications.

The preferred embodiment of the present invention has been described in detail above, but the present invention is not limited to this. Within the scope of the technical concept of the invention, a variety of simple variants of the technical

Figure 5:
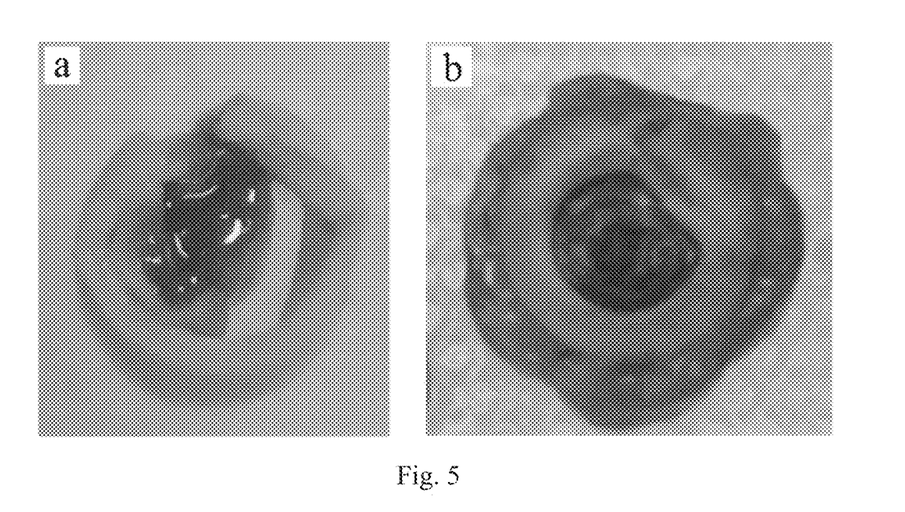
FIG. 5 is a diagram showing comparison for tissue adhesion states of a puncture-resistant artificial blood vessel and a three-layer blood vessel.

| Contrast | Puncture-Resistant Blood Vessel | Three-Layer Blood Vessel |
| --- | --- | --- |
| Characteristics of Outer Layers | The outer layer is of an electrically sprayed structure and is dense and relatively low in priority which is about 60-70%. | The outer layer is of an electrospun structure and a cytoskeleton-like structure and is relatively high in priority which is about 80-90%. |
| Differences of Production Processes | The outer layer is long in electric spray time and is required to be dried directly after reaching a certain thickness. | The middle layer is short in electric spray time and relatively small in thickness, and the outer layer is spun when the middle layer is not completely dried so that the middle layer is tightly combined with the outer layer. |
| Differences of Applications | The artificial blood vessel is used for an in-vivo vascular graft surgery or a heart bypass surgery. | The artificial blood vessel is used for an in-vivo vascular graft surgery, arteriovenous fistulization or a heart bypass surgery. |
| Mechanical Properties | The mechanical properties are higher. | The mechanical properties are lower. |
| Tissue adhesion states | The surface of blood vessel is smooth, the tissue adheres less and is easy to peel the tissue off; The external surface of blood vessel is dense, which can effectively prevent bacteria from invading the blood vessel wall and causing infection (FIG. 5a). | There is a fibrous outer layer on the surface of blood vessels, which promotes the growth of tissue; It can shorten the time of maturation after implantation and prevent the relative slippage of blood vessel and tissue after implantation (FIG. 5b). |

A short segment of 1.6 cm test sample is cut from each of the sample 1 and the sample 2 and is accurate to be ±0.5 mm with millimeter as a unit. Every square centimeter on the outer surface of each sample is punctured for 0-15 times, and the puncture process should be limited within ⅓ of the circumference of the blood vessel. After the samples are repeatedly punctured, the intensities on the circumferences are tested. For every kind of blood vessels, 15 groups of blood vessels are taken, there are 3 samples in each group, and experimental data are recorded and stored as an average value.

The experimental result shows that the average initial radial intensity of the puncture-resistant blood vessel scheme of the invention can be carried out, including the combination of various technical features in any other suitable way. These simple variants and combinations should also be regarded as the contents disclosed by the invention, and all belong to the protection scope of the invention.

What is claimed is:

1. A preparation method for three-layer artificial blood vessel, including the following steps:
    S1: dissolving a macromolecular compound into a solvent to obtain an electrospinning solution with a concentration of 5-30% w/v and an electric-spray solution with a concentration of 10-60% w/v;

S2: placing the electrospinning solution obtained in S1 over a mandrel device and performing electrospinning to obtain a porous electrospun inner layer, drying the inner layer to remove the residual solvent;

S3: with the inner layer obtained in S2 as a receiving surface, performing first electric spray, second electric spray, . . . $n^{th}$ electric spray with the electric-spray solution to obtain a dense middle layer, wherein a process of the first electric spray includes spraying, stopping, spraying, stopping, . . . repeated cycles, a time of the stopping in the process of the first electric spray is 5-20 min; and a time of each of the first electric spray, the second electric spray and the $n^{th}$ electric spray is 5-50 min; and S4: with the dense middle layer obtained in S3 as a receiving surface, performing electrospinning, and then drying to obtain the three-layer artificial blood vessel.

2. The preparation method according to claim 1, in S1, wherein the macromolecular compound is selected from one or more of polycaprolactone, polyurethane and polylactide; and the solvent is selected from one or more of N,N-dimethylformamide, N,N-dimethylacetamide, acetone, tetrahydrofuran and hexafluoroisopropanol; and a weight-average molecular weight of the polycaprolactone, the polylactide and the polyurethane is 10000-1000000.

3. The preparation method according to claim 1, wherein the macromolecular compound for preparing electric-spray solution is selected from one or two of the polycaprolactone and the polyurethane.

4. The preparation method according to claim 1, in S2 and S4, wherein the step of performing electrospinning includes: regulating a distance between a spinning nozzle and a mandrel receiving device to be 5-30 cm; and performing spinning under the conditions that an ambient temperature is 15-70° C., an ambient humidity is 15-70% RH, a voltage is regulated to be 10-50 kV, a feeding speed of the solution is 0.1-5 mL/h, and a rotating speed of a roller is 50-1000 rad/min.

5. The preparation method according to claim 1, wherein an electrospinning time in S2 is 5-30 h and an electrospinning time in S4 is 0.5-15 h.

6. The preparation method according to claim 1, in S3, wherein an n value for the $n^{th}$ electric spray is greater than or equal to 3.

7. The preparation method according to claim 1, in S3, wherein the first electric spray, the second electric spray and the $n^{th}$ electric spray are performed under the conditions including: a feeding speed is 0.1-5 mL/h, a rotating speed of the roller is 50-1000 rad/min, an ambient temperature is 10-50° C., an ambient humidity is 10-60% RH, and a voltage is 5-30 kV.

* * * * *